United States Patent [19]
Sata

[11] Patent Number: 6,034,031
[45] Date of Patent: *Mar. 7, 2000

[54] CATALYST MATERIAL FOR USE IN PRODUCING SUBSTITUTE NATURAL GAS AND METHOD FOR PRODUCING SUBSTITUTE NATURAL GAS

[75] Inventor: Naoaki Sata, Tokyo, Japan

[73] Assignee: NEC Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/715,423

[22] Filed: Sep. 18, 1996

[30] Foreign Application Priority Data

Sep. 18, 1995 [JP] Japan ..................................... 7-238025
Nov. 15, 1995 [JP] Japan ..................................... 7-296569

[51] Int. Cl.⁷ ............................ C07C 27/00; B01J 23/44; B01J 23/40; B01J 23/42
[52] U.S. Cl. .......................... 502/333; 502/339; 502/327; 502/332; 518/715; 518/716
[58] Field of Search ..................................... 502/333, 339, 502/327, 332; 518/716, 715

[56] References Cited

U.S. PATENT DOCUMENTS

| | | |
|---|---|---|
| 4,284,531 | 8/1981 | Simpson et al. ........................ 502/327 |
| 4,288,347 | 9/1981 | Rabinovich et al. .................... 502/327 |
| 4,487,851 | 12/1984 | Heyward et al. ........................ 518/728 |
| 4,492,769 | 1/1985 | Blanchard et al. ...................... 502/327 |
| 4,492,770 | 1/1985 | Blanchard et al. ...................... 502/327 |
| 4,559,364 | 12/1985 | Wood et al. ............................ 518/715 |
| 4,619,947 | 10/1986 | Jackson .................................. 518/716 |
| 5,141,912 | 8/1992 | Ernest et al. ............................ 502/332 |
| 5,149,680 | 9/1992 | Kitson et al. ........................... 502/332 |

FOREIGN PATENT DOCUMENTS

| | | |
|---|---|---|
| 6-248275 | 9/1996 | Japan . |
| 2171925 | 9/1986 | United Kingdom . |

*Primary Examiner*—Walter D. Griffin
*Assistant Examiner*—Thuan D. Dang
*Attorney, Agent, or Firm*—Sughrue, Mion, Zinn, Macpeak & Seas, PLLC

[57] ABSTRACT

A catalyst material produced is for use in producing a substitute natural gas from a source gas containing at least one of carbon dioxide and carbon monoxide, and a reducing gas. The catalyst material contains rhodium and palladium carried on a metal oxide carrier. In producing the substitute natural gas, the source gas containing at least one of carbon dioxide and carbon monoxide, and a reducing gas carried on the metal oxide carrier, are heated under the presence of the catalyst containing rhodium and palladium carried on the metal oxide carrier. It is possible to produce the substitute natural gas highly efficiently at a low temperature not only from carbon monoxide but also from carbon dioxide contained in the source gas.

4 Claims, 1 Drawing Sheet

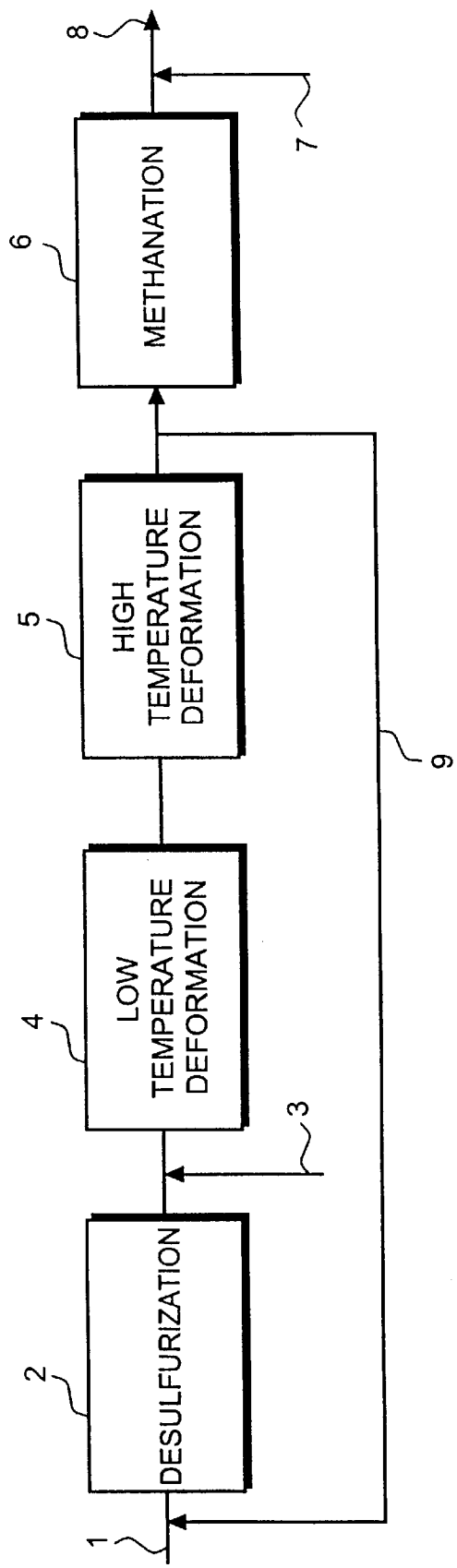

CATALYST MATERIAL FOR USE IN PRODUCING SUBSTITUTE NATURAL GAS AND METHOD FOR PRODUCING SUBSTITUTE NATURAL GAS

BACKGROUND OF THE INVENTION

(1) Field of the Invention

The present invention relates to a catalyst material for use in producing an SNG (Substitute Natural Gas) and a method for producing the SNG, and more particularly to a catalyst material and a method for producing the SNG efficiently at a low temperature from a source gas containing a reducing gas and at least one of carbon dioxide and carbon monoxide. It is possible to produce an SNG gas in a more efficient and simpler manner than when a conventional catalyst is used and not only from carbon monoxide but also from carbon dioxide.

(2) Description of the Related Art

An example of a method for synthesizing SNG from a source gas containing at least one of carbon dioxide and carbon monoxide, and reducing gas such as hydrogen is disclosed in Japanese Patent Application Kokai Publication No. Hei 6-248275. This publication discloses an apparatus for producing a substitute natural gas for use as a city gas in which the main component is methane formed from vapor reformation using fossil hydrocarbon as a source gas and, in which a PSA (Pressure Swing Adsorption) step for separating hydrogen gas by treating the gas produced in a carbon monoxide reformation step is added, and a methanation step for converting to methane a gas produced at a low temperature reformation step and a gas produced from the PSA step is provided.

However, in the method disclosed in Japanese Patent Application Kokai Publication No. Hei 6-248275, it is necessary to supply for the hydrogen gas for the methanation using the PSA step separately, so that the number of steps is increased. In the method disclosed therein, the hydrogen is separately supplied because the activation for methanation of carbon monoxide by methanation catalyst (Ni catalyst) is small. In the Ni based catalyst conventionally used as a catalyst for the production of SNG, the degree of methanation of the carbon dioxide is smaller than that of the carbon monoxide so that, when the carbon monoxide and carbon dioxide co-exist, only the carbon monoxide is methanated unless it is conducted under a temperature above 400° C., which means that practically no methanation occurs in the carbon dioxide. Even if the methanation does occur in the carbon dioxide, the rate of the methanation is extremely small as compared with that in the carbon monoxide.

SUMMARY OF THE INVENTION

An object of the invention, therefore, is to overcome the problems existing in the prior art, and to provide a catalyst material and a method for producing substitute natural gas by using such a catalyst with which, since the rate of methanation of the carbon dioxide is significantly large as compared with that in the conventional catalyst, it is possible to methanate not only the carbon monoxide but also the carbon dioxide efficiently at atmospheric pressure lower than that when a conventional catalyst is used, and also it enables the production of SNG in a simpler manner without separately supplying hydrogen by using steps such as a PSA step.

According to first aspect of the invention, there is provided a catalyst material for use in producing a substitute natural gas from a gas containing at least one of carbon dioxide and carbon monoxide, and a reducing gas, the catalyst material comprising:

a metal oxide carrier; and palladium and rhodium carried by the metal oxide carrier.

According to a second aspect of the invention, there is provided a method for producing a substitute natural gas comprising the steps of:

preparing a catalyst containing palladium and rhodium carried on metal oxides; and heating under the presence of the catalyst a gas containing at least one of carbon dioxide and carbon monoxide, and a reducing gas carried on metal oxides.

The above method for producing a substitute natural gas may further comprises a step of making heat adjustment of a produced gas during the step of heating by using an LPG.

According to the invention, it is possible to produce SNG highly efficiently at a low temperature not only from carbon monoxide but also from carbon dioxide contained in the source gas.

Also, in carrying out the process, there is no need to supply hydrogen separately and only hydrogen in the source gas is used so that, as compared with conventional methods, the production of SNG according to the invention is simpler and yet more highly efficient.

BRIEF DESCRIPTION OF THE DRAWINGS

The above and other objects, features and advantages of the present invention will be apparent from the following description of a preferred embodiment of the invention explained with reference to the accompanying drawings, in which:

The FIGURE is a process diagram for use in explaining a method for producing SNG of an embodiment according to the invention.

PREFERRED EMBODIMENT OF THE INVENTION

A method for synthesizing a catalyst for SNG of an embodiment according to the invention is explained. First, rhodium (III) chloride trihydrate and palladium (II) chloride are diluted in water, and, in this solution, metal oxide which becomes a carrier and which is, for example, activated alumina, is added and heated whereby metal ions, such as rhodium ion and palladium ion, are impregnated into metal oxide. The resulting alumina containing palladium rhodium metal ions are thermally treated under the flow of reducing gas whereby the palladium and rhodium metal ions are reduced down to a simple metal substance, and Pd—Rh/$Al_2O_3$ which is the catalyst for producing SNG according to the invention is synthesized.

It is desirable that the palladium and the rhodium be carried by the metal oxide by 0.1%–10% by weight. In the examples 1 and 2 for the production of SNG explained below, use is made of Pd—Rh/$Al_2O_3$ carrying 1% of Pd and 3% of Rh carried thereon.

An example in which the catalyst according to the invention is used for the production of SNG is explained below.

The FIGURE is a diagram showing the steps of the method in the example.

Hydrocarbon ($C_4H_{10}$ etc.) 1 is used as a starting material. This hydrocarbon is subjected to a desulfurization step 2 and, after the process steam 3 is added followed by the low temperature vapor reformation step 4 and high temperature vapor reformation step 5, a high temperature reformation gas containing $CO_2$, $CO$, $H_2$ as shown in Table 1 is obtained.

The reaction as given in Equation (1) occurs in the low temperature reformation step 4, and reaction as given in Equation (2) is caused to occur in the high temperature reformation step 5 in order to obtain a larger quantity of $H_2$.

$$C_4H_{10} + 4H_2O \rightarrow 4CO + 9H_2 \quad (1)$$

$$CO + H_2O \rightarrow CO_2 + H_2 \quad (2)$$

The high temperature reformation gas obtained by the above step is allowed to flow in Pd—Rh/$Al_2O_3$ catalyst according to the invention at a space velocity of $30000h^{-1}$, at atmospheric, and a temperature of 340° C., CO and $CO_2$ gas in the high temperature reformation gas is methanated (methanation step 6) by $H_2$ in the same gas. The composition ratio (%) of the high temperature reformation gas and the gas produced through the methanation step 6 is shown in Table 1.

Also, as a comparison example, by using a conventional Ni catalyst (Ni/$Al_2O_3$ carrying 4% of nickel on activated alumina) instead of the catalyst according to the invention, the methanation of the high temperature reformation gas is carried out under the same conditions as in example 1, the result of which is shown in Table 2.

TABLE 1

(Example 1)

|  | Methane | Hydrogen | Carbon dioxide | Carbon Monoxide |
|---|---|---|---|---|
| High temp. reformation gas (%) | 9 | 69 | 10 | 12 |
| Formation gas (%) | 95 | 0 | 5 | 0 |

TABLE 2

(Comparison Example 1)

|  | Methane | Hydrogen | Carbon dioxide | Carbon Monoxide |
|---|---|---|---|---|
| High temp. reformation gas (%) | 9 | 69 | 10 | 12 |
| Formation gas (%) | 37 | 46 | 15 | 2 |

Further, by using Ni catalyst with only the change in the temperature condition to 440° C., the methanation of high temperature reformation gas has been carried out in the same way as in Comparison Example 1, the result of which is shown in Table 3.

TABLE 3

(Comparison Example 2)

|  | Methane | Hydrogen | Carbon dioxide | Carbon Monoxide |
|---|---|---|---|---|
| High temp. reformation gas (%) | 9 | 69 | 10 | 12 |
| Formation gas (%) | 91 | 3 | 6 | 0 |

When Table 1 and Table 3 are compared, it can be appreciated that the result obtained using the temperature of 340° C. with the catalyst according to the invention is better than the result obtained using the temperature of 440° C. with the conventional Ni catalyst. From this, it is clear that the catalyst according to the invention enables the methanation of carbon dioxide or carbon monoxide highly efficiently under a temperature lower than that when the conventional catalyst is used.

Where, the catalyst according to the invention is used, only by using CO and $CO_2$ in a high temperature reformation gas and $H_2$ in the same gas, it is possible to methanate not only carbon monoxide but also carbon dioxide in a highly efficient manner, as can be seen in Table 1, under a temperature lower than that in the conventional example. With this, it is possible to reduce the size of a methanation processing apparatus as compared with that of the prior art apparatus, and also to reduce the energy necessary for initial heating.

According to the invention, the gas produced through the methanation step 6 consists of 95% methane and is usable as it is as SNG 8. This gas does not contain carbon monoxide, and can be used, for example, as a city gas having a higher calorie than a conventional city gas of an LPG (Liquefied Petroleum Gas). Depending on uses of gas where heating energy is insufficient or where higher methane impurity is desired, the method may include additional steps such as an additional heating by, for example, an LPG, in a heating adjustment step 7, and an absorption step for un-reacted carbon dioxide. Further, a part of the high temperature reformation gas may well be recycled as a recycling gas 9 for supplying hydrogen to be used in the desulfurization step 2.

In example 1, hydrocarbon is used as a source material, and a steps for obtaining a gas containing $CO_2$, CO, and $H_2$ is included in the method for producing SNG. However, if the gas contains any reducing gas such as $H_2$ and $NH_3$ in the method, such a gas can be used as a source gas for the production of SNG, so that the desulfurization step 2 and the vapor reformation steps 4 and 5 shown in the FIGURE are not necessarily required. An example of a gas containing at least either one of $CO_2$ and CO and a reducing gas such as $H_2$ and $NH_3$ is a gas generated, for example, in an incinerator.

Now, a method for producing SNG of a second example is explained.

TABLE 4

(Example 2)

|  | Methane | Hydrogen | Carbon dioxide | Carbon Monoxide |
|---|---|---|---|---|
| Source gas 1 (%) | 0 | 78 | 11 | 11 |
| Formation gas (%) | 96 | 4 | 0 | 0 |
| Source gas 2 (%) | 0 | 76 | 8 | 16 |
| Formation gas (%) | 96 | 0 | 4 | 0 |
| Source gas 3 (%) | 0 | 76 | 16 | 8 |
| Formation gas (%) | 88 | 0 | 12 | 0 |

Various source gases 1, 2 and 3 which consist of carbon dioxide and carbon monoxide, and hydrogen, are caused to flow at a space velocity of $30000h^{-1}$ and, by using the same catalyst as that used in Example 1, the methanation process has been carried out at atmospheric pressure, and a temperature of 360° C. The result of the process is as shown in Table 4.

Also, in Comparison Example 3, the catalyst alone is replaced to Ni/Al$_2$O$_3$ in Example 1, and the methanation has been carried out using the same source gas and conditions as in Example 2. The results thereof are as given in Table 5.

TABLE 5

(Comparison Example 3)

|  | Methane | Hydrogen | Carbon dioxide | Carbon Monoxide |
|---|---|---|---|---|
| Source gas 1 (%) | 0 | 78 | 11 | 11 |
| Formation gas (%) | 25 | 60 | 15 | 0 |
| Source gas 2 (%) | 0 | 76 | 8 | 16 |
| Formation gas (%) | 41 | 45 | 14 | 0 |
| Source gas 3 (%) | 0 | 76 | 16 | 8 |
| Formation gas (%) | 17 | 63 | 20 | 0 |

As is clear from Tables 4 and 5, when the catalyst according to the invention is used, it is possible to carry out the methanation highly efficiently as long as the gas is one having at least either one of carbon dioxide and carbon monoxide, and reducing gas such as hydrogen, without the need for the gas to be particularly limited to a high temperature reformation gas. The gas produced by methanation can be used as it is as SNG. Of course, if necessary, the gas may be subjected to a heat adjustment step such as a step of adding LPG for increasing heat.

While the invention has been described in its preferred embodiments, it is to be understood that the words which have been used are words of description rather than limitation and that changes within the purview of the appended claims may be made without departing from the true scope of the invention as defined by the claims.

What is claimed is:

1. A combination of materials comprising:

1) a catalyst material for use in producing a substitute natural gas from a substrate gas containing carbon dioxide, 2) a reducing gas, and 3) said substrate gas, said catalyst material in contact with an atmosphere that contains said substrate gas and said reducing gas, said substrate gas and said reducing gas in a concentration and flowing at a flow rate suitable for producing said substitute natural gas, wherein said catalyst material consists of:

a metal oxide carrier; and palladium and rhodium carried by said metal oxide carrier; wherein the total amount of the palladium and rhodium is 4 to 10% by weight.

2. The combination of materials according to claim 1 wherein said metal oxide carrier is Al$_2$O$_3$.

3. A combination of materials according to claim 1, wherein said atmosphere is at a temperature of 360° C. or less.

4. A combination of materials according to claim 1, wherein said atmosphere is at a temperature of 340° C. or less.

* * * * *